US009216937B2

(12) United States Patent
Archer et al.

(10) Patent No.: US 9,216,937 B2
(45) Date of Patent: Dec. 22, 2015

(54) WATER CONCENTRATION REDUCTION PROCESS

(71) Applicant: Rennovia, Inc., Menlo Park, CA (US)

(72) Inventors: Raymond Archer, San Jose, CA (US);
Gary M. Diamond, Menlo Park, CA (US); Eric L. Dias, Belmont, CA (US);
Vincent J. Murphy, San Jose, CA (US);
Miroslav Petro, San Jose, CA (US);
John D. Super, Houston, TX (US)

(73) Assignee: Rennovia Inc., Santa Clara, CA (US)

( * ) Notice: Subject to any disclaimer, the term of this patent is extended or adjusted under 35 U.S.C. 154(b) by 341 days.

(21) Appl. No.: 13/691,588

(22) Filed: Nov. 30, 2012

(65) Prior Publication Data

US 2013/0158255 A1 Jun. 20, 2013

Related U.S. Application Data

(60) Provisional application No. 61/570,614, filed on Dec. 14, 2011.

(51) Int. Cl.
*C07C 55/12* (2006.01)
*C07C 51/377* (2006.01)
(Continued)

(52) U.S. Cl.
CPC ............ *C07C 51/347* (2013.01); *C07C 51/09* (2013.01); *C07C 51/377* (2013.01); *C07C 51/412* (2013.01); *C07C 209/00* (2013.01)

(58) Field of Classification Search
CPC ........ C07C 55/12; C07C 51/377; C07C 69/42
USPC .................................................. 562/515, 523
See application file for complete search history.

(56) References Cited

U.S. PATENT DOCUMENTS 3,671,566 A 6/1972 Decker et al.
3,917,707 A 11/1975 Williams et al.
(Continued)

FOREIGN PATENT DOCUMENTS

JP 53-144506 A 12/1978

OTHER PUBLICATIONS

International Search Report and Written Opinion received for PCT Patent Application No. PCT/US2012/067424, mailed on Jun. 25, 2013, 9 pages.

(Continued)

*Primary Examiner* — Mark Shibuya
*Assistant Examiner* — Janet L Coppins
(74) *Attorney, Agent, or Firm* — Senniger Powers LLP (57) ABSTRACT

The present disclosure relates generally to water concentration reduction processes within an adipic acid process. The present invention also includes process for converting a glucose-containing feed derived from a carbohydrate source to an adipic acid product wherein the process includes the steps of: converting glucose in the feed to a reaction product including a hydrodeoxygenation substrate and a first concentration of water; reducing the concentration of water in the reaction product to produce a feedstock including the hydrodeoxygenation substrate and second concentration of water, wherein the second concentration of water is less than the first concentration of water; and converting at least a portion of the hydrodeoxygenation substrate in the feedstock to an adipic acid product. Processes are also disclosed for producing hexamethylene diamine and caprolactam from the adipic acid product.

29 Claims, 2 Drawing Sheets

(51) Int. Cl.
C07C 69/42 (2006.01)
C07C 51/347 (2006.01)
C07C 51/09 (2006.01)
C07C 209/00 (2006.01)
C07C 51/41 (2006.01)

(56) References Cited

U.S. PATENT DOCUMENTS

| | | | |
|---|---|---|---|
| 4,400,468 | A | 8/1983 | Faber |
| 4,767,856 | A | 8/1988 | Dockner et al. |
| 5,487,987 | A | 1/1996 | Frost et al. |
| 5,516,960 | A | 5/1996 | Robinson |
| 5,900,511 | A | 5/1999 | Sengupta et al. |
| 5,986,127 | A | 11/1999 | Ionkin et al. |
| 6,008,418 | A | 12/1999 | Baur et al. |
| 6,087,296 | A | 7/2000 | Harper |
| 6,147,208 | A | 11/2000 | Achhammer et al. |
| 6,462,220 | B1 | 10/2002 | Luyken et al. |
| 6,521,779 | B1 | 2/2003 | Boschat et al. |
| 6,569,802 | B1 | 5/2003 | Ionkin |
| 8,669,397 | B2 | 3/2014 | Boussie et al. |
| 2007/0215484 | A1 | 9/2007 | Peterson et al. |
| 2010/0317822 | A1 | 12/2010 | Boussie et al. |
| 2010/0317823 | A1* | 12/2010 | Boussie et al. ............. 528/323 |
| 2013/0225785 | A1 | 8/2013 | Dias et al. |
| 2013/0310605 | A1 | 11/2013 | Salem et al. |
| 2013/0345473 | A1 | 12/2013 | Archer et al. |

OTHER PUBLICATIONS

Brown, Jolene M., "Equilibration of D-Glucaric Acid in Aqueous Solution", Master of Science in Chemistry, The University of Waikato, 2007, 192 pages.

Niu et al., "Benzene-Free Synthesis of Adipic Acid", Biotechnol. Prog. vol. 18, Issue. 2, 2002, pp. 201-211.

Gehret et al., "Convenient Large-Scale Synthesis of D-Glucaro-1,4:6,3-dilactone", The Journal of Organic Cchemistry. vol. 74, No. 21, 2009, pp. 8373-8376.

Horton et al., "Conformations of the D-Glucarolactones and D-Glucaric Acid in Solution", Carbohydrate Research, vol. 105, 1982, pp. 95-109.

Huang et al., "Low-Energy Distillation-Membrane Separation Process", Ind. Eng. Chem. Res., vol. 49, No. 8, 2010, pp. 3760-3768.

Novasep Process: Advanced Purification Technologies for Bio-Based Chemicals, Frontiers Bio-Refining 2012, 24 pages.

* cited by examiner

WATER CONCENTRATION REDUCTION PROCESS

CROSS-REFERENCE TO RELATED APPLICATIONS

This application claims the benefit under 35 USC 119(e) of U.S. Provisional Application No. 61/570,614, filed on Dec. 14, 2011, the disclosure of which is hereby incorporated by reference in its entirety.

BACKGROUND OF THE INVENTION

I. Field

The present disclosure relates generally to improved processes for the production of an adipic acid product. More specifically, it relates to processes for converting a glucose-containing feed derived from a carbohydrate source to an adipic acid product wherein the process comprises the steps of: converting glucose in the feed to a reaction product including a hydrodeoxygenation substrate and a first concentration of water; reducing the concentration of water in the reaction product to produce a feedstock including the hydrodeoxygenation substrate and second concentration of water, wherein the second concentration of water is less than the first concentration of water; and converting at least a portion of the hydrodeoxygenation substrate in the feedstock to an adipic acid product.

II. Description of Related Art

Crude oil is currently the source of most commodity and specialty organic chemicals. Many of these chemicals are employed in the manufacture of polymers and other materials. Examples include ethylene, propylene, styrene, bisphenol A, terephthalic acid, adipic acid, caprolactam, hexamethylene diamine, adiponitrile, caprolactone, acrylic acid, acrylonitrile, 1,6-hexanediol, 1,3-propanediol, and others. Crude oil is first refined into hydrocarbon intermediates such as ethylene, propylene, benzene, and cyclohexane. These hydrocarbon intermediates are then typically selectively oxidized using various processes to produce the desired chemical. For example, crude oil is refined into cyclohexane which is then selectively oxidized to "KA oil" which is then further oxidized for the production of adipic acid, an important industrial monomer used for the production of nylon 6,6. Many known processes are employed industrially to produce these petrochemicals from precursors found in crude oil. For example, see Ullmann's Encyclopedia of Industrial Chemistry, Wiley 2009 (7th edition), which is incorporated herein by reference.

For many years there has been an interest in using biorenewable materials as a feedstock to replace or supplement crude oil. See, for example, Klass, Biomass for Renewable Energy, Fuels, and Chemicals, Academic Press, 1998, which is incorporated herein by reference. Moreover, there have been efforts to produce adipic acid from renewable resources using processes involving a combination of biocatalytic and chemocatalytic processes. See, for example, "Benzene-Free Synthesis of Adipic Acid", Frost et al. Biotechnol. Prog. 2002, Vol. 18, pp. 201-211, and U.S. Pat. Nos. 4,400,468, and 5,487,987.

One of the major challenges for converting biorenewable resources such as carbohydrates (e.g. glucose derived from starch, cellulose or sucrose) to current commodity and specialty chemicals is the selective removal of oxygen atoms from the carbohydrate. Approaches are known for converting carbon-oxygen single bonds to carbon-hydrogen bonds. See, for example: U.S. Pat. No. 5,516,960; U.S. Patent App. Pub. US2007/0215484 and Japanese Patent No. 78,144,506. Each of these known approaches suffers from various limitations and we believe that, currently, none of such methods are used industrially for the manufacture of specialty or industrial chemicals.

Industrially scalable methods for the selective and commercially-meaningful conversion of carbon-oxygen single bonds to carbon-hydrogen bonds, especially as applied in connection with the production of chemicals from polyhydroxyl-containing substrates (e.g., glucaric acid), and especially for the production of chemicals from polyhydroxyl-containing biorenewable materials (e.g., glucose derived from starch, cellulose or sucrose) to important chemical intermediates such as adipic acid have been reported in U.S. Patent App. Pubs. US2010/0317822 and US2010/0317823, both of which are hereby incorporated by reference in their entireties. In US2010/0317823, processes for the conversion of glucose-containing feed to an adipic acid product via glucaric acid and/or derivatives thereof are reported. Such processes include the steps of catalytic oxidation of the glucose-containing feed to glucaric acid and/or derivatives thereof followed by catalytic hydrodeoxygenation of glucaric acid and/or derivatives thereof to an adipic acid product. The catalytic oxidation step produces 1 mole of water per mole of glucaric acid on a stoichiometric basis and up to 3 moles of water per mole of glucaric acid derivatives such as lactones. Additionally, the feed to the oxidation reactor typically comprises between about 40% and about 90% water on a weight basis. Applicants have discovered that the efficacy of the subsequent hydrodeoxygenation reaction (to which the glucaric acid-containing product from the oxidation reaction is subjected to produce an adipic acid product) can be significantly beneficially affected by reducing the concentration of water in the feed to the hydrodeoxygenation reaction. The reduction of water also significantly reduces the capital cost of downstream purification equipment and the operating costs associated with such purification.

BRIEF SUMMARY

Briefly, therefore, the present invention is directed to improved processes for preparing an adipic acid product. In accordance with one embodiment, the process comprises the steps of:

a) converting a glucose-containing feed to a reaction product comprising a hydrodeoxygenation substrate and a first concentration of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) producing a feedstock comprising the hydrodeoxygenation substrate and a second concentration of water, wherein the second concentration of water is less than the first concentration of water; and c) converting at least a portion of the hydrodeoxygenation substrate in the feedstock to the adipic acid product. In accordance with another embodiment, the feedstock is produced at least in part from the reaction product having been subjected to a step of reducing the concentration of water thereof relative to the first concentration. In accordance with another embodiment, the step of reducing the concentration of water is carried out using a technique selected from the group consisting of chromatography, distillation, evaporation, extraction, desiccation, membrane separation, pervaporation, and combinations thereof. In accordance with another embodiment, the step of reducing the concentration of water is carried out using membrane separation. In accordance with another embodiment, the step of reducing the concentration of water is carried out using pervaporation. In accordance with another embodiment, the step of reducing the concentration of water is carried out using distillation and pervaporation. In accordance with another embodiment, the step of reducing the concentration of water is carried out using chromatography. In accordance with another embodiment, the step of reducing the concentration of water is carried out using chromatography and extraction. In accordance with another embodiment, the step of reducing the concentration of water is carried out using chromatography and membrane separation. In accordance with another embodiment, the step of reducing the concentration of water is carried out using chromatography and pervaporation. In accordance with another embodiment, the step of reducing the concentration of water is carried out using chromatography, distillation, and pervaporation. In accordance with another embodiment, the chromatography is anion exchange chromatography. In accordance with another embodiment, the anion exchange chromatography utilizes a simulated moving bed (SMB) arrangement. In accordance with another embodiment, the chromatography is carried out in a batch or a continuous process. In accordance with another embodiment, the anion exchange chromatography comprises contacting the reaction product with an anion exchange chromatography medium. In accordance with another embodiment, the anion exchange chromatography comprises eluting C6 mono-acid compounds using a first set of elution conditions, and eluting the glucaric acid and other C2-C6 di-acid compounds using a second set of elution conditions. In accordance with another embodiment, the first set of elution conditions includes the use of an elution solvent comprising up to 30% acetic acid in water. In accordance with another embodiment, the second set of elution conditions includes the use of an elution solvent comprising 30-100% acetic acid in water. In accordance with another embodiment, the anion exchange chromatography medium is selected from the group consisting of Mitsubishi Diaion WA30, Mitsubishi Diaion WA20, Mitsubishi Diaion UBA100S, Mitsubishi Diaion UMA150, Mitsubishi Diaion UMA130J, Mitsubishi Diaion SA21, Finex AS532, Finex AS510, and Dowex Retardion 11A8. In accordance with another embodiment, the anion exchange chromatography medium is selected from the group consisting of Mitsubishi Diaion UBA100S Mitsubishi Diaion UMA150, Mitsubishi Diaion UMA130J, Finex AS532, and Mitsubishi Diaion SA21. In accordance with another embodiment, the anion exchange chromatography medium is selected from the group consisting of Mitsubishi Diaion UBA100S, Finex AS532, and Mitsubishi Diaion UMA150. In accordance with another embodiment, the hydrodeoxygenation substrate comprises a compound of formula I, wherein X is hydroxyl and $R^1$ is independently a salt-forming ion, hydrogen, hydrocarbyl, or substituted hydrocarbyl. In accordance with another embodiment, the hydrodeoxygenation substrate comprises glucaric acid. In accordance with another embodiment, the hydrodeoxygenation substrate comprises D-glucaric acid in equilibria with one or more mono- or di-lactones, and wherein the step of reducing the concentration of water from the reaction product increases the concentration of the one or more of the mono- or di-lactones relative to the equilibrium concentration thereof. In accordance with another embodiment, the hydrodeoxygenation substrate comprises D-glucaric acid, the mono-lactones are selected from the group of glucaro-1,4-lactone and glucaro-3,6-lactone and mixtures thereof, and the di-lactone is glucaro-1,4:3,6-dilactone. In accordance with another embodiment, step a) is an oxidation reaction carried out in the presence of an oxidation catalyst and a source of oxygen. In accordance with another embodiment, the oxidation catalyst comprises a heterogeneous catalyst. In accordance with another embodiment, the oxidation catalyst comprises Pt. In accordance with another embodiment, the oxidation catalyst is a supported catalyst and the catalyst support comprises a material selected from the group consisting of carbon, silica, titania and zirconia. In accordance with another embodiment, step c) is a reduction reaction conducted in the presence of a hydrodeoxygenation catalyst and a halogen source. In accordance with another embodiment, the hydrodeoxygenation catalyst comprises a heterogeneous catalyst. In accordance with another embodiment, the heterogeneous catalyst comprises a d-block metal selected from the group consisting of Ru, Rh, Pd, Pt, and combinations thereof. In accordance with another embodiment, the hydrodeoxygenation catalyst is a supported catalyst and the support is selected from the group consisting of carbon, silica, and zirconia. In accordance with another embodiment, the hydrodeoxygenation catalyst comprises a first metal and a second metal, wherein the first metal is selected from the group consisting of Ru, Rh, Pd, Pt, and combinations thereof, and the second metal is selected from the group consisting of Mo, Ru, Rh, Pd, Ir, Pt, and Au, and wherein the second metal is not the same as the first metal. In accordance with another embodiment, the halogen source comprises an ionic, atomic, and/or molecular form of bromine. In accordance with another embodiment, the halogen source comprises hydrogen bromide. In accordance with another embodiment, the first concentration of water is in the range of about 40% to about 90% on a weight basis. In accordance with another embodiment, the first concentration of water is in the range of about 50% to about 80% on a weight basis. In accordance with another embodiment, the second concentration of water is equal to or less than about 15% on a weight basis. In accordance with another embodiment, the adipic acid product comprises adipic acid. In accordance with another embodiment, the adipic acid product consists essentially of adipic acid.

The present invention is further directed to a process for preparing an adipic acid product, the process comprising:

reacting, in the presence of a hydrodeoxygenation catalyst and hydrogen, a feedstock comprising a hydrodeoxygenation substrate and water in a concentration on a weight basis equal to or less than about 15%, to convert at least a portion of the hydrodeoxygenation substrate to an adipic acid product, wherein the hydrodeoxygenation substrate comprises a compound of formula I:

wherein X is independently hydroxyl, oxo, halo, acyloxy or hydrogen provided that at least one X is not hydrogen and $R^1$ is independently a salt-forming ion, hydrogen, hydrocarbyl, or substituted hydrocarbyl; or a mono- or di-lactone thereof. In accordance with one embodiment, the hydrodeoxygenation substrate comprises glucarolactone and D-glucaric acid. In accordance with another embodiment, the hydrodeoxygenation substrate comprises at least about 40% glucarolactone. In accordance with another embodiment, the hydrodeoxygenation substrate comprises at least about 60% glucarolactone. In accordance with another embodiment, the hydrodeoxygenation substrate comprises at least about 80% glucarolactone. In accordance with another embodiment, the adipic acid product comprises adipic acid. In accordance with another embodiment, the adipic acid product consists essentially of adipic acid.

The present invention is further directed to a process for preparing an adipic acid product, the process comprising the steps of:

a) converting a feed comprising glucose to a reaction product comprising a hydrodeoxygenation substrate comprised of a first concentration of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) modifying the composition of the reaction product to produce a feedstock comprising hydrodeoxygenation substrate comprised of a second concentration of water, wherein the second concentration is water is less than the first concentration of water; and c) subjecting at least a portion of the feedstock to a hydrodeoxygenation reaction to convert at least a portion of the hydrodeoxygenation substrate in the feedstock to the adipic acid product. In accordance with one embodiment, the second concentration of water is equal to or less than about 15% by weight. In accordance with another embodiment, the adipic acid product comprises adipic acid. In accordance with another embodiment, the adipic acid product consists essentially of adipic acid.

The present invention is further directed to a process for producing an adipic acid product, the process comprising the steps of:

a) converting glucose to a hydrodeoxygenation substrate comprising at least about 40% by weight of at least one glucarolactone, and b) converting at least a portion of the hydrodeoxygenation substrate to an adipic acid product. In accordance with one embodiment, the adipic acid product comprises adipic acid. In accordance with another embodiment, the adipic acid product consists essentially of adipic acid.

The present invention is further directed to a process for producing hexamethylene diamine comprising the steps of:

a) converting glucose to a hydrodeoxygenation substrate comprising at least about 40% by weight of at least one glucarolactone, b) converting at least a portion of the hydrodeoxygenation substrate in the presence of not more than about 15% by weight of water to an adipic acid product, and c) converting at least a portion of the adipic acid product to hexamethylene diamine. In accordance with one embodiment, the adipic acid product is adipic acid. In accordance with another embodiment, the hydrodeoxygenation substrate comprises D-glucaric acid and at least one glucarolactone. In accordance with another embodiment, step b) is carried out in the presence of water in a concentration on a weight basis to a feedstock comprising the hydrodeoxygenation substrate which is subject to the conversion equal to or less than about 15%. In accordance with another embodiment, the hydrodeoxygenation substrate comprises at least about 60% glucarolactone. In accordance with another embodiment, the hydrodeoxygenation substrate comprises at least about 80% glucarolactone. In accordance with another embodiment, the concentration of water is obtained at least in part by subjecting a reaction product resulting from the conversion in step a) to chromatography as to so modify the concentration to that as set forth in step b).

The present invention is further directed to a process for producing caprolactam comprising the steps of:

a) converting glucose to a hydrodeoxygenation substrate comprising at least about 40% by weight of at least one glucarolactone, b) converting at least a portion of the hydrodeoxygenation substrate in the presence of not more than about 15% by weight of water to an adipic acid product, and c) converting at least a portion of the adipic acid product to caprolactam. In accordance with one embodiment, the adipic acid product is adipic acid. In accordance with another embodiment, the hydrodeoxygenation substrate comprises D-glucaric acid and at least one glucarolactone. In accordance with another embodiment, step b) is carried out in the presence of water in a concentration on a weight basis to a feedstock comprising the hydrodeoxygenation substrate which is subject to the conversion equal to or less than about 15%. In accordance with another embodiment, the hydrodeoxygenation substrate comprises at least about 60% glucarolactone. In accordance with another embodiment, the hydrodeoxygenation substrate comprises at least about 80% glucarolactone. In accordance with another embodiment, the concentration of water is obtained at least in part by subjecting a reaction product resulting from the conversion in step a) to chromatography as to so modify the concentration to that as set forth in step b).

The present invention is further directed to a process for preparing an adipic acid product, the process comprising the steps of:

a) converting a glucose-containing feed to a reaction product comprising a hydrodeoxygenation substrate and a first concentration of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) producing a feedstock comprising the hydrodeoxygenation substrate and a second concentration of water, wherein the second concentration of water is less than the first concentration of water and wherein at least a portion of the feedstock is reaction product the concentration of water of which has been reduced by removing at least a portion of the water therefrom; and c) converting at least a portion of the hydrodeoxygenation substrate in the feedstock to the adipic acid product. In accordance with one embodiment, the step of reducing the concentration of water is carried out using chromatography. In accordance with another embodiment, the step of reducing the concentration of water is carried out using chromatography and extraction. In accordance with another embodiment, the step of reducing the concentration of water is carried out using chromatography and membrane separation. In accordance with another embodiment, the step of reducing the concentration of water is carried out using chromatography and pervaporation. In accordance with another embodiment, the step of reducing the concentration of water is carried out using chromatography, distillation, and pervaporation. In accordance with another embodiment, the chromatography is anion exchange chromatography. In accordance with another embodiment, the anion exchange chromatography utilizes a simulated moving bed (SMB) arrangement. In accordance with another embodiment, the chromatography is carried out in a batch or a continuous process. In accordance with another embodiment, the anion exchange chromatography comprises contacting the reaction product with an anion exchange chromatography medium. In accordance with another embodiment, the anion exchange chromatography comprises eluting C6 mono-acid compounds using a first set of elution conditions, and eluting the glucaric acid and other C2-C6 di-acid compounds using a second set of elution conditions. In accordance with another embodiment, the first set of elution conditions includes the use of an elution solvent comprising up to 30% acetic acid in water. In accordance with another embodiment, the second set of elution conditions includes the use of an elution solvent comprising 30-100% acetic acid in water. In accordance with another embodiment, the anion exchange chromatography medium is selected from the group consisting of Mitsubishi Diaion WA30, Mitsubishi Diaion WA20, Mitsubishi Diaion UBA100S, Mitsubishi Diaion UMA150, Mitsubishi Diaion UMA130J, Mitsubishi Diaion SA21, Finex AS532, Finex AS510, and Dowex Retardion 11A8. In accordance with another embodiment, the anion exchange chromatography medium is selected from the group consisting of Mitsubishi Diaion UBA100S Mitsubishi Diaion UMA150, Mitsubishi Diaion UMA130J, Finex AS532, and Mitsubishi Diaion SA21. In accordance with another embodiment, the anion exchange chromatography medium is Mitsubishi Diaion UBA100S, Finex AS532, or Mitsubishi Diaion UMA150. In accordance with another embodiment, the hydrodeoxygenation substrate comprises a compound of formula I, wherein X is hydroxyl and $R^1$ is independently a salt-forming ion, hydrogen, hydrocarbyl, or substituted hydrocarbyl. In accordance with another embodiment, the hydrodeoxygenation substrate comprises glucaric acid. In accordance with another embodiment, the adipic acid product comprises adipic acid. In accordance with another embodiment, the hydrodeoxygenation substrate comprises D-glucaric acid in equilibria with one or more mono- or di-lactones, and wherein the step of removing at least a portion of the water from the reaction product increases the concentration of the one or more of the mono- or di-lactones relative to the equilibrium concentration thereof. In accordance with another embodiment, the hydrodeoxygenation substrate comprises D-glucaric acid, the mono-lactones are selected from the group of glucaro-1,4-lactone and glucaro-3,6-lactone and mixtures thereof, and the di-lactone is glucaro-1,4:3,6-dilactone. In accordance with another embodiment, the first concentration of water is in the range of about 40% to about 90% on a weight basis. In accordance with another embodiment, the first concentration of water is in the range of about 50% to about 80% on a weight basis. In accordance with another embodiment, the second concentration of water is equal to or less than about 15% on a weight basis.

The present invention is further directed to a process for preparing an adipic acid product, the process comprising the steps of:

a) preparing a feedstock solution comprising a hydrodeoxygenation substrate and not more than about 15% by weight of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof; and b) converting at least a portion of the hydrodeoxygenation substrate in the feedstock to the adipic acid product. In accordance with one embodiment, the conversion step comprises reacting the hydrodeoxygenation substrate with hydrogen in the presence of a catalyst. In accordance with another embodiment, the reaction is conducted in the presence of a catalyst and a source of halogen. In accordance with another embodiment, the catalyst is a heterogeneous catalyst. In accordance with another embodiment, the halogen is bromine. In accordance with another embodiment, the source of halogen is hydrogen bromide.

The present invention is further directed to a process for preparing hexamethylene diamine, the process comprising the steps of:

a) preparing a feedstock solution comprising a hydrodeoxygenation substrate and not more than about 15% by weight of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) converting at least a portion of the hydrodeoxygenation substrate in the feedstock to adipic acid product; and c) converting at least a portion of the adipic acid product to hexamethylene diamine. In accordance with one embodiment, the adipic acid product is adipic acid.

The present invention is further directed to a process for preparing caprolactam, the process comprising the steps of:

a) preparing a feedstock solution comprising a hydrodeoxygenation substrate and not more than about 15% by weight of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) converting at least a portion of the hydrodeoxygenation substrate in the feedstock to adipic acid product; and c) converting at least a portion of the adipic acid product to caprolactam. In accordance with one embodiment, the adipic acid product is adipic acid.

DETAILED DESCRIPTION

The following description sets forth exemplary methods, parameters and the like. It should be recognized, however, that such description is not intended as a limitation on the scope of the present invention.

As used herein, the term "glucaric acid" collectively refers to D-glucaric acid ($C_6H_{10}O_8$) and/or derivatives thereof. The glucaric acid may be substantially pure D-glucaric acid or may exist in a mixture that includes any amount of one or more derivatives thereof. Similarly, the glucaric acid may be a substantially pure derivative of D-glucaric acid such as, for example, D-glucaro-1,4-lactone or may include any amount of one or more other derivatives of D-glucaric acid and/or the acid itself. Derivatives of D-glucaric acid include "glucarolactones," which include mono- or di-lactones of D-glucaric acid such as D-glucaro-1,4-lactone, D-glucaro-6,3-lactone, and D-glucaro-1,4:6,3-dilactone. Other derivatives include salts, esters, ketones, and halogenated forms of the acid.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl, substituted cycloalkyl and the like.

As used herein, the term "about" means approximately, in the region of, roughly, or around. When the term "about" is used in conjunction with a numerical range, it modifies that range by extending the boundaries above and below the numerical values set forth.

The present invention provides processes for preparing an adipic acid product, the process comprising the steps of:

a) converting a glucose containing feed to a reaction product comprising a hydrodeoxygenation substrate and a first concentration of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) producing from the reaction product a feedstock comprising the hydrodeoxygenation substrate and a second concentration of water, wherein the second concentration of water is less than the first concentration of water; and c) converting at least a portion of the hydrodeoxygenation substrate in the feedstock to the adipic acid product.

I. Feedstocks

Glucose can be obtained from various carbohydrate-containing sources including conventional biorenewable sources such as corn grain (maize), wheat, potato, cassava and rice as well as alternative sources such as energy crops, plant biomass, agricultural wastes, forestry residues, sugar processing residues and plant-derived household wastes. More generally, biorenewable sources that may be used in accordance with the present invention include any renewable organic matter that includes a source of carbohydrates such as, for example, switch grass, miscanthus, trees (hardwood and softwood), vegetation, and crop residues (e.g., bagasse and corn stover). Other sources can include, for example, waste materials (e.g., spent paper, green waste, municipal waste, etc.). Carbohydrates such as glucose may be isolated from biorenewable materials using methods that are known in the art. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007; Furia, *Starch in the Food Industry, Chapter 8, CRC Handbook of Food Additives* 2nd Edition, CRC Press 1973. See also chapters devoted to Starch, Sugar and Syrups within *Kirk-Othmer Encyclopedia of Chemical Technology* 5th Edition, John Wiley and Sons 2001. Also, processes to convert starch to glucose are known in the art, see, for example, Schenck, "Glucose and Glucose containing Syrups" in *Ullmann's Encyclopedia of Industrial Chemistry*, Wiley-VCH 2009. Furthermore, methods to convert cellulose to glucose are known in the art, see, for example, Centi and van Santen, *Catalysis for Renewables*, Wiley-VCH, Weinheim 2007; Kamm, Gruber and Kamm, *Biorefineries-Industrial Pro-*

*cesses and Products*, Wiley-VCH, Weinheim 2006; Shang-Tian Yang, *Bioprocessing for Value-Added Products from Renewable Resources New Technologies and Applications*, Elsevier B. V. 2007.

II. Preparation of Glucaric Acid

In accordance with the present invention, glucose in a feed is converted to a reaction product containing glucaric acid and a first concentration of water and a feedstock is produced from the reaction product and comprises the glucaric acid and a second concentration of water, the second concentration being less than the first concentration, which feedstock is then subjected to a hydrodeoxygenation reaction to produce an adipic acid product. Recently, the preparation of glucaric acid from glucose using oxidation catalysts has been reported in copending application Ser. No. 12/814,188, filed on Jun. 11, 2010 (published as US2010/0317823), which is hereby incorporated by reference in its entirety. As disclosed therein, glucose may be converted to glucaric acid in high yield by reacting glucose with oxygen in the presence of the oxidation catalyst and in the absence of added base according to the following reaction:

Catalytic selectivity can be maintained to attain glucaric acid yield in excess of 70% and up to about 90%. In various preferred embodiments, the oxidation catalyst can be selected from among the catalysts described in US2010/0317823. In some embodiments, the oxidation catalyst includes a heterogeneous catalyst. In some embodiments the oxidation catalyst includes Pt. In various preferred embodiments, the oxidation catalyst is a supported catalyst. Catalyst supports include materials such as carbon, silica, titania, zirconia, or mixtures thereof.

The reaction product of the oxidation step will, as described above, yield glucaric acid in considerable and heretofore unexpected fraction. As previously described, glucaric acid may exist as mixtures of D-glucaric acid and glucarolactones, or principally or solely as either. The glucaric acid resulting from the oxidation step constitutes the hydrodeoxygenation substrate which is particularly amenable to the production of an adipic acid product as hereinafter described. Glucarolactones which may be present in the reaction mixture resulting from the oxidation step include mono and di-lactones such as D-glucaro-1,4-lactone, D-glucaro-6,3-lactone, and D-glucaro-1,4:6,3-dilactone. One unexpected advantage of higher concentrations of glucarolactones is further improvement in the economics of the hydrodeoxygenation step resulting from a reduction in the amount of water produced.

In addition to producing D-glucaric acid and glucarolactones, the glucose oxidation reaction product may produce other compounds including C2-C6 di-acid compounds such as, for example, tartaric acid, oxalic acid, or mixtures thereof, and C6 mono-acid compounds such as gluconic acid, keto-gluconic acids, glucuronic acid, or mixtures thereof. The mono-acid compounds may be separated from the di-acid compounds. Once separated, the mono-acid compounds may be recycled to the oxidation reactor and the di-acid compounds may be carried as constituents of the feedstock to the hydrodeoxygenation step. A preferred method of separation is chromatography. In some preferred embodiments, the method of separation is ion exchange chromatography, or still more preferably anion exchange chromatography. As discussed below, the separation step may also function to reduce the concentration of water so as to produce a feedstock which then may be directly subjected to the hydrodeoxygenation step.

III. Reducing the Concentration of Water

In accord with the present invention, the reaction product of the glucose oxidation reaction will include a hydrodeoxygenation substrate comprising glucaric acid and a first concentration of water. Unexpected improvements in processes for the production of adipic acid product result from modifying the concentration of water such that a feedstock to the hydrodeoxygenation reaction is comprised of hydrodeoxygenation substrate of the reaction product and water, wherein the concentration of water in the feedstock (the "second concentration of water") is less than the first concentration of water.

Generally, the concentration of water in the glucose oxidation reaction product (the "first concentration of water") is in the range of about 40% to about 90% on a weight basis. More typically, the concentration of water in the reaction product is in the range of about 50% to about 80%. As described generally heretofore, the reaction product is then subjected to modification such that a feedstock to the hydrodeoxygenation reaction is produced, wherein the water concentration in the feedstock is less than the first concentration. More specifically, in various preferred embodiments, the second concentration of water is equal to or less than about 15% on a weight basis.

In some embodiments, reducing the concentration of the water in the feedstock relative to that in the oxidation reaction product is further beneficial in that it is possible to more easily accommodate the use of a weak carboxylic acid as a solvent for the hydrodeoxygenation reaction. See, e.g., US2010/0317823. A preferred weak carboxylic acid is acetic acid. The reduced water concentration coupled with the use of a weak carboxylic acid solvent for the hydrodeoxygenation reaction provide further benefits such as even shorter reaction times, more improved selectivities, and still higher overall yields of adipic acid product. It is therefore desirable to subject the reaction product of the glucose oxidation reaction to modification such that a reduction in the concentration of water is achieved so that a weak carboxylic acid can be added for use as a solvent in the hydrodeoxygenation reaction, thus producing a preferred feedstock for the hydrodeoxygenation reaction. In general, the concentration of weak carboxylic acid solvent in the hydrodeoxygenation reaction (on a weight basis) is typically at least about 40%, or preferably at least about 50%, or more preferably at least about 60%, or even at least about 70%.

In various embodiments, a reduced concentration of water in the feedstock relative to the concentration of water in the reaction product may be effected using a variety of techniques including chromatography, distillation, evaporation, extraction, desiccation, membrane separation (for example, a pervaporation membrane separation), adding glucaric acid, or any combination thereof. In some embodiments, the water concentration may be reduced by a membrane separation such as, for example, a pervaporation membrane separation. In other embodiments, the water concentration may be reduced by distillation, such as fractional distillation. In still other embodiments, the water concentration may be reduced by a solvent flash (evaporation) followed by a membrane separation such as, for example, a pervaporation membrane separation. Pervaporation may also be referred to in the art as "membrane vapor permeation." A combination distillation-pervaporation system for separating water from acetic acid is known in the art, for example, as described in "Low-Energy Distillation-Membrane Separation Process" Huang, et al., Ind. Eng. Chem. Res., 49 (8), pp. 3760-3768 (2010), which is incorporated herein by reference, and may be used to reduce the water concentration as described heretofore. In other embodiments, the water concentration may be reduced using distillation and pervaporation.

As described more fully below, in accord with the present invention, it is demonstrated that chromatography can be used as a method to reduce the water concentration in the glucose oxidation product, introduce a weak carboxylic acid solvent, and separate glucaric acid (including other C2-C6 di-acids, if any) from the C6-mono-acids, so as to produce an unexpectedly valuable feedstock for use in the hydrodeoxygenation reaction. As additionally described below, reducing the concentration of water in the reaction product may drive the equilibrium from an acyclic hydrodeoxygenation substrate toward the formation of cyclic lactones which are believed to be beneficial in the hydrodeoxygenation reaction.

In some embodiments, the water concentration is reduced in conjunction with separation of glucaric acid and other C2-C6 di-acid compounds from C6 mono-acid compounds resulting from the oxidation reaction by subjecting the oxidation reaction product to chromatography. In some embodiments, the water concentration is reduced by chromatography and extraction. In other embodiments, the water concentration is reduced by chromatography and membrane separation, such as pervaporation. In other embodiments, the water concentration is reduced by chromatography, distillation, and pervaporation. In a preferred embodiment, anion exchange chromatography is employed to effect the above described reduction and separations. Anion exchange chromatography may be used to separate the mono-acid compounds from the glucaric acid and other di-acid compounds, if any, using an anion exchange medium that has a different retention strength for glucaric acid and other C2-C6 di-acid compounds in comparison to its retention strength for C6 mono-acid compounds. For example, in some embodiments, the oxidation reaction product may be contacted with an anion exchange chromatography column under isocratic or gradient elution conditions that initially selectively retain the glucaric acid and other C2-C6 di-acid compounds on the anion exchange medium and elute the C6 mono-acid compounds using a first set of elution conditions. For example, it has been discovered that the first set of elution conditions may include use of an elution solvent comprising up to 30% acetic acid in water, or preferably up to about 20% acetic acid in water. The eluted C6 mono-acid compounds may then be recycled to the oxidation reactor. After elution of the mono-acid compounds using the first set of elution conditions, the glucaric acid and other C2-C6 di-acid compounds, if any, may be eluted from the anion exchange chromatography medium using a second set of elution conditions. The second set of elution conditions may include the use of an elution solvent including more than 30% acetic acid in water, more typically about 40-90% acetic acid in water, or about 50-90% acetic acid in water, thereby reducing the water concentration as compared to that initially present in the oxidation reaction product. In some embodiments, the water concentration in the oxidation product after the anion-exchange chromatography separation may be further reduced using a second water concentration reducing technique including a second chromatography separation, distillation, evaporation, extraction, desiccation, membrane separation, pervaporation, or any combination thereof. As described above, the concentration of water remaining after the second water concentration reducing technique is preferably equal to or less than about 15% on a weight basis.

Suitable anion exchange chromatography media may include weak anion or strong anion exchange resins. In some embodiments, the anion exchange chromatography medium is Mitsubishi Diaion WA30, Mitsubishi Diaion WA20, Mitsubishi Diaion UBA100S, Mitsubishi Diaion UMA150, Mitsubishi Diaion UMA130J, Mitsubishi Diaion SA21, Dowex Retardion 11A8, Finex AS510, or Finex AS532. In some preferred embodiments, the anion exchange chromatography medium is Mitsubishi Diaion UBA100S, Mitsubishi Diaion UMA150, Finex AS532, or Mitsubishi Diaion UMA130J. In other preferred embodiments, the anion exchange chromatography medium is Mitsubishi Diaion UBA100S, Finex AS532, or Mitsubishi Diaion UMA150. Typically, the anion exchange chromatography medium is packed into a chromatographic separation apparatus which may include one or more chromatography columns. In some embodiments, the anion exchange chromatography is carried out using simulated moving bed (SMB) chromatography. In general, the anion exchange chromatography medium may encompass a variety of resin particle sizes and functional group loadings when used to reduce the water concentration from the glucose oxidation reaction product.

Generally, the anion exchange chromatography medium is conditioned prior to the reducing of the water concentration from the oxidation reaction product. For weak anion resins, the conditioning may include contacting the anion exchange chromatography medium with aqueous acid solutions to protonate the resin to the desired form, for example acetate or formate. For some strong anion resins containing chloride, the chloride may be converted to the hydroxide form by contacting the resin with multiple bed volumes (e.g., 20 or more bed volumes) of a NaOH solution followed by washing the resin with multiple bed volumes (e.g., 10 or more bed volumes) of de-ionized water. The hydroxide form may then be contacted with an aqueous acid such as acetic or formic acid to produce the desired anion form through acid-base neutralization. For other strong anion resins containing chloride, the resins may be conditioned in situ by performing a blank aqueous acid gradient elution with multiple bed volumes (e.g., 20 or more bed volumes).

After the one or more chromatography columns have been packed with the desired anion exchange chromatography medium, and the anion exchange chromatography medium has been conditioned, the oxidation reaction product may be loaded onto the column to perform the separation and remove the at least some of the water. The anion exchange chromatography may be carried out in a batch, semi-continuous or continuous process. C6 mono-acid compounds may then be eluted using a first set of elution conditions, and glucaric acid and other C2-C6 di-acid compounds may then be eluted using a second set of elution conditions. A variety of elution conditions may be employed, for example, the first set of elution conditions may include the use of an elution solvent comprising up to 30% acetic acid in water. Following the first set of elution conditions, the second set of elution conditions may include, for example, an elution solvent comprising 30-100% acetic acid in water.

During any of the water concentration reducing steps described herein, as the concentration of water in the hydrodeoxygenation substrate is reduced to equal to or less than about 15% by weight, there is an equilibrium shift that results in a higher concentration of lactones. For example, not wishing to be bound by theory, it is believed that various mono- and di-lactones are present in equilibrium with glucaric acid in aqueous solution, including for example, D-glucaro-1,4- lactone, D-glucaro-6,3-lactone, and D-glucaro-1,4:6,3-dilactone. More generally, the water concentration reducing steps drive the equilibrium from the acyclic, D-glucaric acid to cyclic mono- and/or di-lactone compounds. At such concentrations of water, the hydrodeoxygenation substrate typically comprises lactones in the range of about 40% to about 100% by weight of the hydrodeoxygenation substrate, preferably at least about 60% and more preferably at least about 80%. The aqueous equilibria of glucarolactones and D-glucaric acid is known in the art as described, for example, in "Conformations of the D-Glucarolactones and D-Glucaric Acid in Solution" Horton et al., Carbohydrate Research, 105, pp. 95-109 (1982) and "Equilibration of D-Glucaric Acid in Aqueous Solution" Brown, Masters Thesis in Chemistry, The University of Waikato (2007).

Moreover, processes have been developed to quantitatively convert D-glucaric acid in solution to one or more lactones and recover a substantially pure lactone stream. For example see "Convenient Large-Scale Synthesis of D-Glucaro-1,4:6, 3-dilactone" Gehret et al., J. Org. Chem., 74 (21), pp. 8373-8376 (2009). Also, lactones such as L-threo-4-deoxy-hex-4-enaro-6,3-lactone and L-erythro-4-deoxy-hex-4-enaro-6,3-lactone may form from the thermal decomposition of D-Glucaro-1,4:6,3-dilactone. Consequently, one could incorporate into the process the additional step of cyclization/ dehydration, wherein the conversion of D-glucaric acid to lactone is effected and water may be separated from the reaction product of this step by any of the water removal processes described herein.

Therefore, in various embodiments, the hydrodeoxygenation substrate comprises D-glucaro-1,4-lactone. In these and other embodiments, the hydrodeoxygenation substrate comprises D-glucaro-6,3-lactone. Still further, in these and other embodiments, the hydrodeoxygenation substrate comprises D-glucaro-1,4:6,3-dilactone. In these and other embodiments, the hydrodeoxygenation substrate comprises L-threo-4-deoxy-hex-4-enaro-6,3-lactone. Still even further, in these and other embodiments, the hydrodeoxygenation substrate comprises L-erythro-4-deoxy-hex-4-enaro-6,3-lactone. In these embodiments, the hydrodeoxygenation substrate composition comprises a mixture of D-glucaro-6,3-lactone, D-glucaro-1,4-lactone and D-glucaro-1,4:6,3-dilactone, wherein the lactone mixture is in the range of 40% to about 100% of the composition of the hydrodeoxygenation substrate, preferably at least about 60% and more preferably at least about 80%.

The above described water concentration reduction techniques enables the production of a feedstock useful for the hydrodeoxygenation reaction that comprises hydrodeoxygenation substrate and a second concentration of water; more preferably, one which contains no more than about 15% by weight of water. The feedstock, comprised of hydrodeoxygenation substrate and a second concentration of water, can then be advantageously converted to an adipic acid product.

IV. Preparation of an Adipic Acid Product

In accordance with the present invention, a feedstock comprising hydrodeoxygenation substrate from the oxidation reaction product and water in a second concentration may be introduced into a second reactor system in which at least a portion of the hydrodeoxygenation substrate is converted to adipic acid product.

The hydrodeoxygenation of a hydrodeoxygenation substrate to produce an adipic acid product is disclosed in copending application Ser. No. 12/814,188, filed on Jun. 11, 2010 (published as US2010/0317823), which is hereby incorporated by reference in its entirety. The hydrodeoxygenation reaction is as follows:

wherein X is independently hydroxyl, oxo, halo, acyloxy or hydrogen provided that at least one X is not hydrogen; $R^1$ is independently a salt-forming ion, hydrogen, hydrocarbyl, or substituted hydrocarbyl; or a mono- or di-lactone thereof. In some embodiments, the compound of formula II is the adipic acid product. In preferred embodiments of the present invention, the compound of formula II is primarily, or almost solely, adipic acid.

In various embodiments, the hydrodeoxygenation substrate is catalytically hydrodeoxygenated in the presence of hydrogen, a halogen source, and a hydrodeoxygenation catalyst. In some embodiments, the hydrodeoxygenation catalyst includes a heterogeneous catalyst. In some embodiments, the heterogeneous catalyst includes a d-block metal such as Ru, Rh, Pd, Pt, or combinations thereof. In some preferred embodiments, the hydrodeoxygenation catalyst is a supported catalyst and the support includes carbon, silica, zirconia, or mixtures thereof. In some preferred embodiments, the hydrodeoxygenation catalyst includes a first metal and a second metal, wherein the first metal includes Ru, Rh, Pd, Pt, or mixtures thereof, and the second metal includes Mo, Ru, Rh, Pd, Ir, Pt, Au, or mixtures thereof, and wherein the second metal is not the same as the first metal. In some embodiments, the halogen source includes an ionic, atomic, and/or molecular form of bromine. In preferred embodiments, the hydrodeoxygenation substrate is catalytically hydrodeoxygenated in the presence of hydrogen, a source of bromine and a hydrodeoxygenation catalyst as described in US2010/0317823. In preferred embodiments, the halogen source or source of bromine includes hydrogen bromide.

In various embodiments, the adipic acid product includes adipic acid. In preferred embodiments, the adipic acid product consists essentially of adipic acid. In accordance with the present invention, reducing the concentration of water to not more than about 15% by weight results in higher yields of adipic acid.

An adipic acid product may be recovered from the hydrodeoxygenation reaction mixture by one or more conventional methods known in the art including, for example, solvent extraction, crystallization, evaporative processes, or any combination in any order thereof.

V. Downstream Chemical Products

Various methods are known in the art for conversion of adipic acid to downstream chemical products or intermediates including adipate esters, polyesters, adiponitrile, hexamethylene diamine (HMDA), caprolactam, caprolactone, 1,6-hexanediol, aminocaproic acid, and polyamide such as nylons. For conversions from adipic acid, see for example, without limitation, U.S. Pat. Nos. 3,671,566, 3,917,707, 4,767,856, 5,900,511, 5,986,127, 6,008,418, 6,087,296, 6,147,208, 6,462,220, 6,521,779, 6,569,802, and Musser, "Adipic Acid" in Ullmann's Encyclopedia of Industrial Chemistry, Wiley-VCH, Weinheim, 2005. Conversion of adipic acid to downstream chemical products is also discussed in US2010/0317823.

In various embodiments, an adipic acid product is converted to adiponitrile wherein the adipic acid product is prepared in accordance with the present invention. Adiponitrile can be used industrially for the manufacture of hexamethylene diamine, see Smiley, "Hexamethylenediamine" in Ullman's Encyclopedia of Industrial Chemistry, Wiley-VCH 2009. Therefore, in further embodiments, an adipic acid product is converted to hexamethylene diamine wherein the adipic acid product is prepared in accordance with the present invention. In some embodiments, hexamethylene diamine is produced by a) converting glucose to a hydrodeoxygenation substrate comprising at least about 40% by weight of at least one glucarolactone; b) converting at least a portion of the hydrodeoxygenation substrate in the presence of not more than about 15% by weight of water to an adipic acid product, and c) converting at least a portion of the adipic acid product to hexamethylene diamine. In some embodiments, the hexamethylene diamine is produced by the steps of:

a) preparing a feedstock solution comprising a hydrodeoxygenation substrate and not more than about 15% by weight of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) converting at least a portion of the hydrodeoxygenation substrate in the feedstock to adipic acid product; and c) converting at least a portion of the adipic acid product to hexamethylene diamine.

In preferred embodiments, the adipic acid product used to produce hexamethylene diamine is adipic acid. In other preferred embodiments, the hydrodeoxygenation substrate includes D-glucaric acid and at least one glucarolactone. In other preferred embodiments, step b) is carried out in the presence water in a concentration on a weight basis to a feedstock comprising the hydrodeoxygenation substrate which is subject to the conversion equal to or less than about 15%. In other preferred embodiments, the hydrodeoxygenation substrate comprises at least about 80% glucarolactone. In preferred embodiments, the concentration of water is obtained at least in part by subjecting a reaction product resulting from the conversion is step a) to chromatography as to so modify the concentration to that as set forth in step b). In preferred embodiments, the adipic acid product used to produce hexamethylene diamine is adipic acid.

In other embodiments, an adipic acid product is converted to caprolactam wherein the adipic acid product is prepared in accordance with the present invention. The caprolactam formed can be further used for the preparation of polyamides by means generally known in the art. Specifically, caprolactam can be further used for the preparation of nylon 6. See, for example Kohan, Mestemacher, Pagilagan, Redmond, "Polyamides" in Ullmann's Encyclopedia of Industrial Chemistry, Wiley-VCH, Weinheim, 2005. In some embodiments, caprolactam is produced by the steps of: a) converting glucose to a hydrodeoxygenation substrate comprising at least about 40% by weight of at least one glucarolactone, b) converting at least a portion of the hydrodeoxygenation substrate in the presence of not more than about 15% by weight of water to an adipic acid product, and c) converting at least a portion of the adipic acid product to caprolactam. In some embodiments, caprolactam is produced by the steps of: a) preparing a feedstock solution comprising a hydrodeoxygenation substrate and not more than about 15% by weight of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) converting at least a portion of the hydrodeoxygenation substrate in the feedstock to adipic acid product; and c) converting at least a portion of the adipic acid product to caprolactam.

In preferred embodiments, the adipic acid product used to produce caprolactam is adipic acid.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

I. General Procedures

Glucaric acid to adipic acid reactions were conducted in 1 mL glass vials housed in a pressurized vessel in accordance with the procedure described in Example 1, below. Product yields were determined using mass spectrometry relative to a $d_8$-adipic acid internal standard. The catalyst was prepared according to the procedures described in US2010/0317823.

II. Anion-Exchange Resins for Separations and Water Removal

The testing of commercially-available, anion-exchange resins was conducted using a Gilson preparative liquid chromatograph fitted with either a) a 2 cm ID×3 cm length column packed with the candidate resin (Examples 2 and 3), or b) a 21.3 cm ID×250 cm length column packed with the candidate resin (Examples 4-7). The detection technique was an ELSD connected on-line after a UV detector. Flow rates, mobile phase compositions and gradients are described in the sections below. Experiments were conducted at room temperature.

Exemplary anion-exchange resins tested in the Examples are listed in Table 1. All resins were conditioned prior to testing. All weak anion resins were received in the free-base form and contacted with aqueous acid solutions served to protonate the resin to the desired form (acetate or formate). Type I strong anion resins Mitsubishi Diaion UBA100S and Mitsubishi Diaion UMA150 were transformed from the chloride forms (as received) to the hydroxide forms by contacting with 20 bed volumes of 1N NaOH solution followed by 10 bed volumes of de-ionized water. The resins were loaded in the hydroxide form with aqueous acid contact (acetic acid or formic acid) giving the desired anion form through acid-base neutralization. Type II strong anion resin Mitsubishi Diaion SA21A and Type I strong anion resin Dowex Retardion 11A8 were received in the chloride form and conditioned in situ by performing a blank aqueous acid gradient elution (typically >20 bed volumes total elution).

TABLE 1

Exemplary Anion-Exchange Resins

| Resin ID | Manufacturer | Type | Matrix | Mean particle size/ μm | Uniformity coefficient | Functional group loading/ eq $L^{-1}$ | Moisture/ wt % |
|---|---|---|---|---|---|---|---|
| Amberlite IRA-67 | Rohm & Haas | Weak anion, tertiary amine | Acrylic | 632 | 1.49 | 1.72 | 60 |
| Diaion UBA100S | Mitsubishi | Strong anion, Type 1 | PS/DVB | 174 | 1.04 | 1.43 | 48 |
| Diaion WA10 | Mitsubishi | Weak anion, tertiary amine | Acrylic | >350 | <1.6 | >1.2 | 63-69 |
| Diaion WA20 | Mitsubishi | Weak anion, secondary amine | PS/DVB | 440 | 1.4 | 2.7 | 43 |
| Diaion WA30 | Mitsubishi | Weak anion, tertiary amine | PS/DVB | 490 | 1.6 | 1.6 | 50 |
| Diaion SA21A | Mitsubishi | Strong anion, Type II | PS/DVB | >400 | <1.6 | >0.8 | 55-65 |
| Dowex Retardion 11A8 | Dowex | Strong anion, Type I: weak acid (poly(acrylic acid)) | PS/DVB | ~250 | | | 45 |
| Diaion UMA150 | Mitsubishi | Strong anion, Type 1 | PS/DVB | 220 | 1.05 | 1.58 | 43 |
| AS532 | Finex | Strong anion, Type II | PS/DVB | 370 | | 1.06 | 55 |
| AS510 | Finex | Strong anion, Type I | PS/DVB | 300 | | 1.3 | 49 |

III. Analytical Procedures

Fractions collected from the testing of anion-exchange resins were reanalyzed by HPLC or by ion chromatography separation.

HPLC Separation

Separations were carried out using an Agilent 1100 HPLC instrument with evaporative light scattering detector (ELSD). Sample injection volume was 10 μL. Samples were separated using a Neptune HILIC 150×4.6 mm column (5 μm particle size, 100 Å pore diameter, ES Industries Part#135221-NPN-SI) using gradient elution.

Ion Chromatography Separation

Ion chromatography separations were performed using a parallel Dionex ICS-3000 with the following components: 1) AS autosampler, 2) DP quaternary pump, 3) EG eluent generator (KOH, two KOH cartridges), 4) column compartment with two 10 μL sample loops and two Dionex IonPac AS11-HC 2×250 mm analytical columns plus two Dionex IonPac AG11-HC 2×50 mm guard columns, 5) detector compartment with two ASRS 300 suppressors and conductivity detectors, and 6) ESA Corona CAD detector after each conductivity detector.

Ion chromatography separations were performed with 0.22 μm filtered and degassed 18.2 MΩ-cm water at 25° C. Samples were diluted to approximately 5 mM for analysis. This concentration enables detection by both conductivity and CAD with parabolic calibration (concentration=$ax^2+bx$, where x=analytical area). Reducing concentration to <0.5 mM enables linear calibration by conductivity at the expense of CAD detection. Typically, glucose, gluconic acid, glucaric acid, tartaric acid, glucuronic acid, 5-ketogluconic acid, and oxalic acid were analyzed under gradient elution conditions.

Example 1

Effect of Water Concentration on Hydrodeoxygenation of Glucaric Acid to Adipic Acid 20 mg catalyst (1.7% Pt-0.6% Rh/Davisil 635) was dispensed into a 1.2 mL vial. Glacial acetic acid was added followed by a 10% water/acetic acid solution according to Table 1. 50 μL of an acetic acid solution containing 1.2 M HBr and 1.6 M D-glucaric acid was added bringing the final solution volume to 100 μL. The vials were transferred to a pressure reactor which was then sealed, purged with nitrogen and pressurized with hydrogen to 820 psig at room temperature. The reactor was agitated and heated to 160° C. for 90 minutes. After 90 minutes, the reactor was cooled to room temperature, vented, and purged with nitrogen prior to being unsealed. Adipic acid yields were determined by mass spectrometry relative to a $d^8$-adipic acid internal standard.

TABLE 2

Experimental Data for Example 1

| Experiment Number | Acetic Acid Addition (μL) | 10% H2O/ Acetic Acid Addition (μL) | Solvent Composition | | Adipic Acid Yield (%) |
|---|---|---|---|---|---|
| | | | Acetic Acid (%) | Water (%) | |
| 1 | 50 | 0 | 100 | 0 | 76 |
| 2 | 20 | 30 | 97 | 3 | 70 |
| 3 | 0 | 50 | 95 | 5 | 58 |

The results in Table 2 demonstrate that reducing the concentration of water in the hydrodeoxygenation reaction of glucaric acid increased the yields of adipic acid.

Example 2

Reduction of Water Concentration During the Separation of Components by Ion-Exchange Chromatography on Commercial Resins Aqueous solutions of glucose, gluconic acid, D-glucaric acid, and tartaric acid were injected individually into selected resins using the Gilson preparative LC system. Mobile phase components were water and acetic acid.

The first seven resins listed in Table 1 were tested with the following method:
1) flow rates 2-5 mL/min,
2) gradient elution from 5-95% acetic acid in water,
3) injections of 1 mL (200 mg/mL solutions), and
4) fractions were collected and re-analyzed by HPLC and/or ion chromatography.

The results illustrated that glucose was not retained under any conditions, and gluconic acid (a C6 mono-acid), eluted at lower acetic acid concentrations (5-30% acetic acid), and D-glucaric acid and tartaric acid (an "other C6 di-acid") eluted at higher acetic acid concentrations (50% acetic acid). These results demonstrate that, in accordance with the present invention, a reduction in the concentration of water in the oxidation reaction product can be attained in combination with separation of unwanted products by employing ion exchange chromatography wherein acetic acid is used under specific conditions to enable the separation and accumulation of D-glucaric acid in acetic acid from C6 mono-acids and unreacted glucose.

Example 3

Reduction of Water Concentration During the Separation of Components by Ion-Exchange Chromatography on Select Commercial Resins The following resins were selected based on the results in Example 2: Mitsubishi Diaion UBA100S, DOWEX Retardion 11A8, and Mitsubishi Diaion SA21.

Aqueous solutions of glucose, gluconic acid, D-glucaric acid, and tartaric acid were injected individually into the Gilson preparative LC system. Mobile phase components were water and acetic acid.

A gradient elution condition was deployed using the following conditions:
1) flow rate 5 mL/min,
2) gradient elution from 5-50% acetic acid in water,
3) injections of 0.25 mL (200 mg/mL solutions), and
4) fractions were collected and re-analyzed by HPLC and/or ion chromatography. Blank runs were injected prior to and after each sample.

The order of retention of the components were tartaric acid>glucaric acid>gluconic acid>glucose. The results again illustrated that glucose was not retained under any conditions, and gluconic acid (a C6 mono-acid) eluted at lower acetic acid concentrations (5-30% acetic acid), and glucaric acid and tartaric acid (an "other C6 di-acid") eluted at higher acetic acid concentrations (50% acetic acid). D-glucaric acid and tartaric acid eluted completely using 50% acetic acid in water. Again, these results demonstrate that, in accordance with the present invention, a reduction in the concentration of water in the oxidation reaction product can be attained in combination with separation of unwanted products by employing ion exchange chromatography wherein acetic acid is used under specific conditions to enable the separation and accumulation of D-glucaric acid in acetic acid from C6 mono-acids and unreacted glucose.

Example 4

Reduction of Water Concentration During the Separation of Components by Ion-Exchange Chromatography on Commercial Resins Aqueous solutions of gluconic acid, D-glucaric acid, and tartaric acid were injected individually into the Gilson preparative LC system. Mobile phase components were water and acetic acid.

The resin selected for separations tests was Mitsubishi UMA150. Isocratic elution conditions were deployed using the following acetic acid/water mobile phase compositions: 20% acetic acid in water; 30% acetic acid in water; 40% acetic acid in water; 50% acetic acid in water; 70% acetic acid in water; 80% acetic acid in water; and 90% acetic acid in water.

The mobile phase compositions were deployed using the following conditions:
1) flow rate 20 mL/min,
2) injections of 1.00 mL (800 mg/mL solutions), and
3) fractions were collected and re-analyzed by HPLC and/or ion chromatography The results illustrated that gluconic acid, a mono acid, eluted at low acetic acid concentrations (20% acetic acid) and that D-glucaric acid and tartaric acid (an "other C6 di-acid") may be eluted at higher acetic acid concentrations (40-90% acetic acid). These results demonstrate that components of interest may be separated and the water concentration may be reduced from the initial D-glucaric acid solvent composition of 100% water to about 90% acetic acid/10% water using catch and release ion exchange chromatography, which solution would be a more preferred hydrodeoxygenation substrate.

Example 5

Reduction of Water Concentration During the Separation of Gluconic and Glucaric Acid by Ion-Exchange Chromatography on Mitsubishi Diaion UBA100S 1.00 mL of an aqueous mixture of gluconic acid (12 wt %) and D-glucaric acid (26 wt %) was injected into the Gilson preparative LC system.

The following gradient elution conditions were employed:
1) flow rate 20 mL/min,
2) 1-50 min: 15% acetic acid/85% water,
3) 50.1-150 min: 50% acetic acid/50% water, and
4) fractions were collected and re-analyzed by HPLC.

Figure 1:
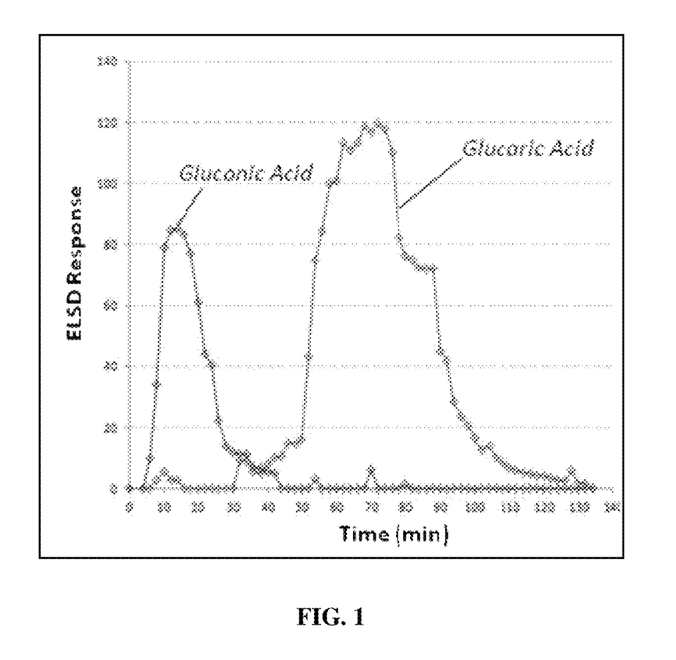
FIG. 1 depicts the separation of gluconic and glucaric acid by catch and release ion-exchange chromatography on a Mitsubishi Diaion UBA100S resin while reducing the water concentration from 100% water to 50% acetic acid/50% water.

The results are shown in FIG. 1. This result demonstrates that components of interest may be separated and the water concentration may be reduced from the initial glucaric acid solvent composition of 100% water to about 50% acetic acid/50% water using catch and release ion exchange chromatography.

Example 6

Reduction of Water Concentration During the Separation of Gluconic and Glucaric Acid by Ion-Exchange Chromatography on Mitsubishi Diaion UMA150

1.00 mL of an aqueous mixture of gluconic acid (12 wt %) and D-glucaric acid (26 wt %) was injected into the Gilson preparative LC system.

The following gradient elution conditions were employed:
1) flow rate 20 mL/min,
2) 1-10 min: 10% acetic acid/90% water,
3) 10.1-90 min: 50% acetic acid/50% water, and
4) fractions were collected and re-analyzed by HPLC.

Figure 2:
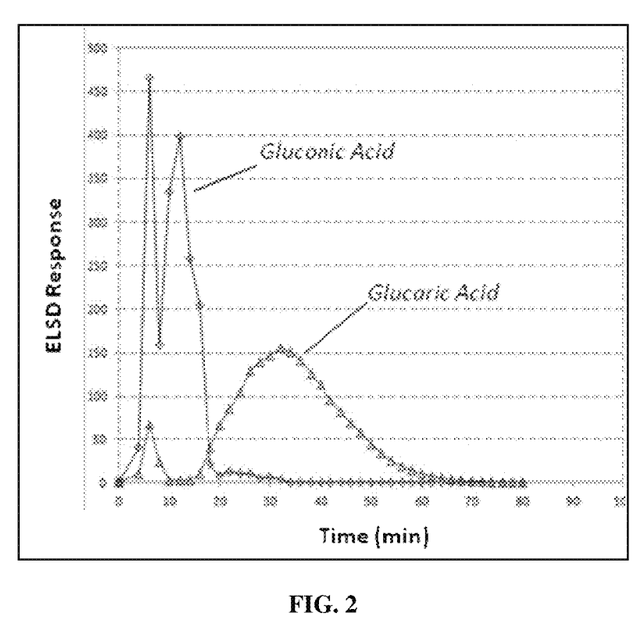
FIG. 2 depicts the separation of gluconic and glucaric acid by catch and release ion-exchange chromatography on a Mitsubishi Diaion UMA150 resin while reducing the water concentration from 100% water to 50% acetic acid/50% water.

The results are shown in FIG. 2. This result demonstrates that components of interest may be separated and the water concentration may be reduced from the initial glucaric acid solvent composition of 100% water to about 50% acetic acid/50% water using catch and release ion exchange chromatography.

Example 7

Capture of Glucaric Acid Equilibrium Mixture and Release of Glucarolactones An aqueous solution of D-glucaric acid (1 ml of 200 mg/ml solution) was injected into the HPLC loaded with Mitsubishi Diaion UBA100S resin and eluted using the following gradient elution conditions:
1) flow rate 5 mL/min,
2) gradient elution:
   a) 2 minutes at 5% acetic acid in water,
   b) 6 minute ramp from 5-95% acetic acid in water,
   c) 1 minute ramp from 95-5% acetic acid in water, and
   d) 10 minutes at 5% acetic acid in water.

Fractions 1 and 2 were analyzed using an Agilent LC fitted with a hypercarb column connected to a Corona CAD detector. The separation was conducted at 45° C. using the following gradient elution conditions:
1) flow rate 1.2 mL/min,
2) gradient elution:
   a) 1 minute at 0.1% formic acid in water,
   b) 7 minute ramp to 60% water and 40% of a solution containing (50% MeOH/49.9 water %/0.1% formic acid), and
   c) 9 minute ramp to 0.1% formic acid in water.

The LC traces for Fractions 1 and 2 contained a mixture of 1,4 and 3,6-monolactones of glucaric acid only. No evidence for the presence of acyclic glucaric acid could be detected by LC-CAD. Peaks were assigned by comparison with calibration standards. These results demonstrate yet another embodiment of the present invention in which one can preferentially separate and collect lactones if desired for feed of the lactones to the hydrodeoxygenation step as the hydrodeoxygenation substrate.

What is claimed is:
1. A process for preparing an adipic acid product, the process comprising the steps of:
   a) converting a glucose-containing feed to a reaction product comprising a hydrodeoxygenation substrate and having a first concentration of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) reducing the first concentration of water of the reaction product comprising the hydrodeoxygenation substrate to produce a feedstock comprising the hydrodeoxygenation substrate and having a second concentration of water, wherein the second concentration of water is less than the first concentration of water and is equal to or less than about 15% on a weight basis; and c) converting at least a portion of the hydrodeoxygenation substrate in the feedstock to the adipic acid product of formula II:

wherein $R^1$ is defined above.

2. The process of claim 1, wherein the step of reducing the concentration of water is carried out using a technique selected from the group consisting of chromatography, distillation, evaporation, extraction, desiccation, membrane separation, pervaporation, and combinations thereof.

3. The process of claim 1, wherein the step of reducing the concentration of water is carried out using anion exchange chromatography.

4. The process claim 3, wherein the anion exchange chromatography utilizes a simulated moving bed (SMB) arrangement.

5. The process of claim 3, wherein the reaction product of step a) comprises C6 mono-acid compounds, glucaric acid, and other C2-C6 di-acid compounds and wherein the anion exchange chromatography comprises eluting C6 mono-acid compounds using a first set of elution conditions, and eluting the glucaric acid and other C2-C6 di-acid compounds using a second set of elution conditions.

6. The process of claim 5, wherein the first set of elution conditions includes the use of an elution solvent comprising up to 30% acetic acid in water and the second set of elution conditions includes the use of an elution solvent comprising 30-100% acetic acid in water.

7. The process of claim 3, wherein the anion exchange chromatography medium is selected from the group consisting of Mitsubishi Diaion WA30, Mitsubishi Diaion WA20, Mitsubishi Diaion UBA100S, Mitsubishi Diaion UMA150, Mitsubishi Diaion UMA130J, Mitsubishi Diaion SA21, Finex AS532, Finex AS510, and Dowex Retardion 11A8.

8. The process of claim 1, wherein the hydrodeoxygenation substrate comprises a compound of formula I, wherein X is hydroxyl and $R^1$ is independently a salt-forming ion, hydrogen, hydrocarbyl, or substituted hydrocarbyl.

9. The process of claim 1, wherein the hydrodeoxygenation substrate comprises glucaric acid.

10. The process of claim 1, wherein the hydrodeoxygenation substrate comprises D-glucaric acid in equilibria with one or more mono- or di-lactones, and wherein the step of reducing the concentration of water from the reaction product increases the concentration of the one or more of the mono- or di-lactones relative to the equilibrium concentration thereof, wherein the mono-lactones are selected from the group of glucaro-1,4-lactone and glucaro-3,6-lactone and mixtures thereof, and the di-lactone is glucaro-1,4:3,6-dilactone.

11. A process for preparing an adipic acid product, the process comprising the steps of:

a) converting a glucose-containing feed to a reaction product comprising a hydrodeoxygenation substrate and having a first concentration of water, wherein the hydrodeoxygenation substrate comprises a compound of formula I:

wherein each X is independently hydroxyl, oxo, acyloxy or hydrogen provided that at least one X is not hydrogen and $R^1$ is independently a salt-forming ion, hydrogen, hydrocarbyl, or substituted hydrocarbyl, or a mono- or di-lactone thereof;

b) reducing the first concentration of water of the reaction product comprising the hydrodeoxygenation substrate to produce a feedstock comprising the hydrodeoxygenation substrate and having a second concentration of water, wherein the second concentration of water is less than the first concentration of water and wherein reducing the concentration of water is carried out using chromatography; and c) converting at least a portion of the hydrodeoxygenation substrate in the feedstock to the adipic acid product of formula II:

wherein $R^1$ is defined above.

12. The process of claim 11, wherein the chromatography is anion exchange chromatography.

13. The process of claim 10, wherein step a) is an oxidation reaction carried out in the presence of a heterogeneous oxidation catalyst and a source of oxygen.

14. The process of claim 13, wherein the heterogeneous oxidation catalyst comprises Pt.

15. The process of claim 14, wherein the heterogeneous oxidation catalyst is a supported catalyst and the catalyst support comprises a material selected from the group consisting of carbon, silica, titania and zirconia.

16. The process of claim 14, wherein step c) is a reduction reaction conducted in the presence of a heterogeneous hydrodeoxygenation catalyst and a halogen source.

17. The process of claim 16, wherein the heterogeneous hydrodeoxygenation catalyst comprises a d-block metal selected from the group consisting of Ru, Rh, Pd, Pt, and combinations thereof.

18. The process of claim 17, wherein the heterogeneous hydrodeoxygenation catalyst is a supported catalyst and the support is selected from the group consisting of carbon, silica, and zirconia.

19. The process of claim 16, wherein the heterogeneous hydrodeoxygenation catalyst comprises a first metal and a second metal, wherein the first metal is selected from the group consisting of Ru, Rh, Pd, Pt, and combinations thereof, and the second metal is selected from the group consisting of Mo, Ru, Rh, Pd, Ir, Pt, and Au, and wherein the second metal is not the same as the first metal.

20. The process of claim 17, wherein the halogen source comprises hydrogen bromide.

21. The process of claim 20, wherein the adipic acid product is adipic acid.

22. The process of claim 9, wherein the first concentration of water is in the range of about 40% to about 90% on a weight basis.

23. The process of claim 22, wherein the adipic acid product is adipic acid.

24. The process of claim 1, wherein the process further comprises recovering the adipic acid product from the hydrodeoxygenation reaction mixture.

25. The process of claim 1, wherein the second concentration of water is less than about 5% on a weight basis.

26. The process of claim 11, wherein the hydrodeoxygenation substrate comprises glucaric acid and the adipic acid product comprises adipic acid.

27. The process of claim 11, wherein step a) is an oxidation reaction carried out in the presence of a heterogeneous oxidation catalyst and a source of oxygen and wherein step c) is a reduction reaction conducted in the presence of a heterogeneous hydrodeoxygenation catalyst and a halogen source.

28. The process of claim 27, wherein the heterogeneous oxidation catalyst comprises Pt and the heterogeneous oxidation catalyst is a supported catalyst and the catalyst support comprises a material selected from the group consisting of carbon, silica, titania and zirconia;

wherein the heterogeneous hydrodeoxygenation catalyst comprises a d-block metal selected from the group consisting of Ru, Rh, Pd, Pt, and combinations thereof and the heterogeneous hydrodeoxygenation catalyst is a supported catalyst and the support is selected from the group consisting of carbon, silica, and zirconia; and wherein the halogen source comprises hydrogen bromide.

29. The process of claim 11, wherein the hydrodeoxygenation substrate comprises at least about 80% glucarolactone.

* * * * *

UNITED STATES PATENT AND TRADEMARK OFFICE
CERTIFICATE OF CORRECTION

PATENT NO.       : 9,216,937 B2
APPLICATION NO.  : 13/691588
DATED            : December 22, 2015
INVENTOR(S)      : Raymond Archer et al.

It is certified that error appears in the above-identified patent and that said Letters Patent is hereby corrected as shown below:

In the Claims:

Column 25, Claim 1, Lines 25-33

" I"

Should read

"--  II --"

Signed and Sealed this
Twenty-sixth Day of July, 2016

Michelle K. Lee
*Director of the United States Patent and Trademark Office*

CERTIFICATE OF CORRECTION (continued)

U.S. Pat. No. 9,216,937 B2

In the Claims:

Column 26, Claim 11, Lines 45-52

" I "

Should read

-- II --